United States Patent
Brouwer et al.

(10) Patent No.: US 6,542,626 B1
(45) Date of Patent: Apr. 1, 2003

(54) METHOD AND APPARATUS FOR ADAPTING IMAGING SYSTEM OPERATION BASED ON PIXEL INTENSITY HISTOGRAM

(75) Inventors: Dean W. Brouwer, Muskego, WI (US); Larry Y. L. Mo, Waukesha, WI (US); Steven C. Miller, Pewaukee, WI (US)

(73) Assignee: General Electric Company, Waukesha, WI (US)

( * ) Notice: Subject to any disclaimer, the term of this patent is extended or adjusted under 35 U.S.C. 154(b) by 0 days.

(21) Appl. No.: 09/434,817

(22) Filed: Nov. 5, 1999

(51) Int. Cl.[7] .............................................. G06K 9/00
(52) U.S. Cl. ...................................... 382/128; 382/168
(58) Field of Search .............................. 382/128, 168, 382/170, 317, 132; 600/437–442; 128/662.02

(56) References Cited

U.S. PATENT DOCUMENTS

| | | | |
|---|---|---|---|
| 5,042,077 A | | 8/1991 | Burke .......................... 382/51 |
| 5,224,177 A | * | 6/1993 | Doi et al. .................... 382/168 |
| 5,313,948 A | * | 5/1994 | Murashita et al. ...... 128/662.02 |
| 5,594,807 A | * | 1/1997 | Liu ............................. 382/128 |
| 5,662,113 A | * | 9/1997 | Liu ......................... 128/600.07 |
| 5,732,705 A | | 3/1998 | Yokoyama et al. .... 128/660.07 |
| 5,793,883 A | | 8/1998 | Kim et al. ................... 382/128 |
| 5,954,653 A | * | 9/1999 | Hatfield et al. ............. 600/443 |
| 6,011,862 A | * | 1/2000 | Doi et al. .................... 382/132 |
| 6,238,341 B1 | * | 5/2001 | Mullen ........................ 600/437 |
| 6,227,073 B1 | * | 8/2001 | Bolorforsh et al. ......... 600/437 |
| 6,322,505 B1 | * | 11/2001 | Hossack et al. ............ 600/437 |

FOREIGN PATENT DOCUMENTS

| | | |
|---|---|---|
| EP | 0 544 328 A | 6/1993 |
| EP | 0 772 158 A | 5/1997 |

* cited by examiner

Primary Examiner—Jon Chang
Assistant Examiner—Brian Le
(74) Attorney, Agent, or Firm—Ostrager Chong & Flaherty LLP

(57) ABSTRACT

A method and an apparatus for optimizing operating parameters in an ultrasound imaging system in response to the occurrence of predetermined changes in the pixel intensity histogram of successive image frames. In the method, changes in the pixel intensity histogram of successive image frames are monitored and when the detected changes indicate probe movement, re-optimization of the operating parameters is automatically triggered. In the course of re-optimization, mapping, compression, scaling or beamforming parameters can be adjusted based on pixel intensity histogram characteristics determined by the system computer.

23 Claims, 5 Drawing Sheets

METHOD AND APPARATUS FOR ADAPTING IMAGING SYSTEM OPERATION BASED ON PIXEL INTENSITY HISTOGRAM

FIELD OF THE INVENTION

This invention generally relates to ultrasound imaging for the purpose of medical diagnosis. In particular, the invention relates to methods for imaging tissue and blood flow by detecting ultrasonic echoes reflected from a scanned region of interest in a human body.

BACKGROUND OF THE INVENTION

Conventional ultrasound scanners are capable of operating in different imaging modes. In the B mode, two-dimensional images can be generated in which the brightness of each display pixel is derived from the value or amplitude of a respective acoustic data sample representing the echo signal returned from a respective focal position within a scan region.

In the B-mode imaging, an ultrasound transducer array is activated to transmit beams focused at respective focal positions in a scan plane. After each transmit firing, the echo signals detected by the transducer array elements are fed to respective receive channels of a receiver beamformer, which converts the analog signals to digital signals, imparts the proper receive focus time delays and sums the time-delayed digital signals. For each transmit firing, the resulting vector of raw acoustic data samples represents the total ultrasonic energy reflected from a succession of ranges along a receive beam direction. Alternatively, in multiline acquisition two or more receive beams can be acquired following each transmit firing.

In conventional B-mode imaging, each vector of raw acoustic data samples is envelope detected and the resulting acoustic data is compressed (e.g., using a logarithmic compression curve). The compressed acoustic data is output to a scan converter, which transforms the acoustic data format into a video data format suitable for display on a monitor having a conventional array of rows and columns of pixels. This video data is referred herein as "raw pixel intensity data". The frames of raw pixel intensity data are mapped to a gray scale for video display. Each gray-scale image frame, hereinafter referred to as "gray-scale pixel intensity data", is then sent to the video monitor for display.

A conventional ultrasound imaging system typically employs a variety of gray maps, which are simple transfer functions of raw pixel intensity data to display gray-scale values. Multiple gray maps are supported so that different maps may be used depending on the range of pixel intensities. For example, if a given application tends to generate mainly low raw pixel intensities, then a gray map which dedicates more gray-scale values to low raw pixel intensity values is desired since it improves the contrast across this range. Therefore, it is typical to default to a different gray map depending on the application. However, this is not always effective since the user can scan any anatomy in any application, acoustic data varies from patient to patient, and the raw pixel intensity values depend on other system settings such as dynamic range. Due to these factors, the gray maps tend to be conservative with respect to how many gray-scale values are dedicated to the anticipated primary pixel intensity range.

A "one-touch" automatic tissue optimization (ATO) method is known which allows the system user to adjust the contrast by pressing a so-called ATO button on an operator interface. When the user has positioned the probe over the anatomy of interest, depressing an ATO button triggers the host computer inside the ultrasound imaging system to retrieve the current frame of raw pixel intensity data, analyze its pixel intensity histogram within a user-specified region of interest (ROI), and then automatically scale and/or shift the gray mapping (i.e., raw pixel intensity to gray-scale pixel intensity mapping) such that pre-defined "optimal" upper and lower gray-scale levels map to some upper and lower bounds of the pixel intensity histogram respectively. The ultimate goal is to more fully utilize the available gray-scale levels (256 levels for an 8-bit display system) to display the pixel intensity data, thereby improving the display tissue contrast.

In the one-touch ATO approach, however, if the probe or ROI is moved to another location, the user is required to press the ATO button again to re-optimize the gray mapping based on the new tissue data. A more fully automated version of this feature is desirable because during a clinical exam, the sonographer often needs to move the probe around a lot to find or study multiple anatomical features, and in many clinical applications such as vascular and surgical applications, both of the sonographer's hands are already busy or sterilized.

SUMMARY OF THE INVENTION

The present invention is a method and an apparatus for optimizing operating parameters in an ultrasound imaging system in response to the occurrence of predetermined changes in the pixel intensity histogram of successive image frames. In the course of re-optimization, mapping, compression, scaling or beamforming parameters can be adjusted based on pixel intensity histogram characteristics determined by the computer.

The method in accordance with the preferred embodiment comprises the steps of monitoring changes in the pixel intensity histogram of successive image frames, which may be indicative of probe movements, and when appropriate, automatically triggering re-optimization of the operating parameters. The assumptions are as follows: (1) as long as the pixel intensity histogram is changing (the ultrasound probe is moving), the sonographer is doing general looking around; and (2) when the pixel intensity histogram has evolved into a new, stable form for a preset amount of time (the probe is held still again), the sonographer has found something interesting to look at. In response to satisfaction of these two conditions, the relevant operating parameters are re-optimized. In accordance with one preferred embodiment, the compression curve and/or the gray mapping are automatically optimized (e.g., set to values which optimize contrast in the displayed image). In accordance with other preferred embodiments, the beamforming parameters or the scaling parameters can be automatically adjusted to display an image in a zoom mode. In accordance with the preferred embodiments, the pixel intensity histogram analysis and the re-optimization of the operating parameters in dependence on the histogram analysis results are performed by the host computer incorporated in the ultrasound imaging system.

It should be noted that in practice, probe motion may not always cause large changes in the pixel intensity histogram, especially if the probe remains in good contact with the skin surface and the underlying tissue characteristics happen to be quite uniform. If the pixel intensity histogram has changed a lot, however, chances are that significant probe motion has occurred. Thus, the triggering mechanism for image optimization is based on pixel intensity histogram changes and not probe motion per se. In the case of the data compression curve and gray mapping, as long as the pixel intensity histogram remains relatively unchanged, there is no need for re-optimization regardless of probe motion.

The invention makes ultrasound imaging systems easier to use. Examination times will be shortened due to less downtime spent optimizing the mapping parameters. The invention will also facilitate standardization or reproducibility of exams done by different sonographers. Finally, the invention allows "hands free" scanning during surgical, vascular and other applications where both hands are already busy or sterile.

BRIEF DESCRIPTION OF THE DRAWINGS

FIG. 4 comprising

DETAILED DESCRIPTION OF THE PREFERRED EMBODIMENTS

Figure 1:
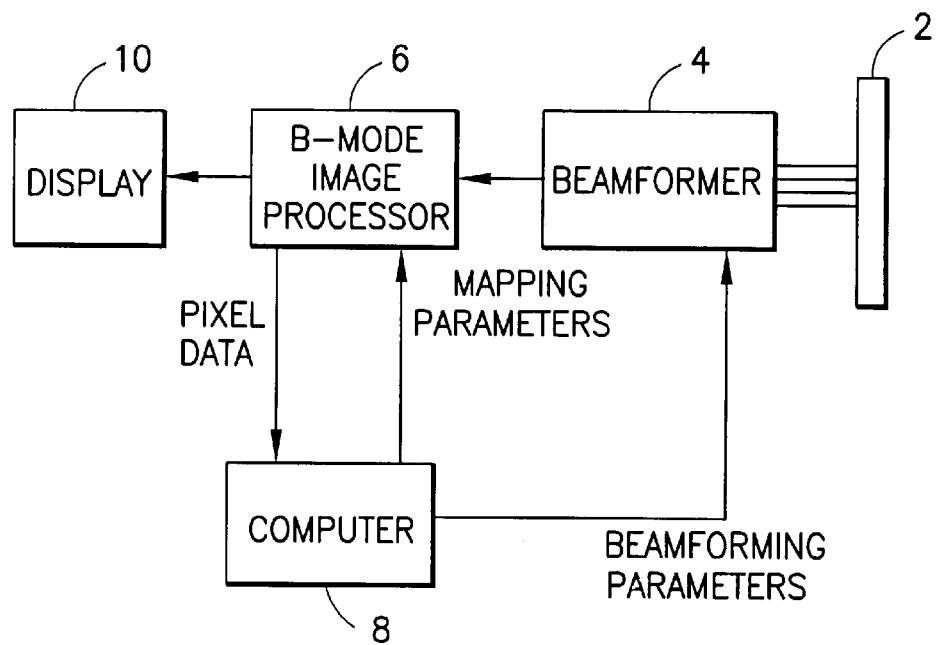
FIG. 1 is a block diagram generally showing an ultrasound imaging system in accordance with the preferred embodiment of the invention.

Referring to FIG. 1, an ultrasound imaging system in accordance with one preferred embodiment of the invention comprises a transducer array 2, a beamformer 4, a B-mode image processor 6, a computer 8 and a display monitor 10. The transducer array 2 comprises a multiplicity of transducer elements which are activated-by a transmitter in beamformer 4 to transmit an ultrasound beam focused at a transmit focal position. The return RF signals are detected by the transducer elements and then dynamically focused at successive ranges along a scan line by a receiver in beamformer 4 to form a receive vector of raw acoustic data samples. The beamformer output data (I/Q or RF) for each scan line is passed through a B-mode image processor 6, which processes the raw acoustic data into pixel image data in a format suitable for display by the display monitor 10.

System control is centered in a computer 8, which accepts operator inputs through an operator interface (not shown), analyzes the acquired data and controls the various subsystems based on operator inputs and the results of data analysis. In accordance with the preferred embodiments, the host computer 8 performs one or more of the following functions: (1) providing transmit and beamforming parameters to the beamformer 4; (2) providing a new gray map to the B-mode image processor 6; (3) retrieving an image frame from memory, re-scaling that image frame and then sending the re-scaled image to the display monitor for display in a zoom mode; and (4) providing a new data compression curve to the B-mode image processor 6. Preferably, the gray map, beamforming parameters and compression curves are provided in the form of lookup tables stored in random access memory. Although FIG. 1 depicts separate paths for the communications to and from the host computer 8, it will be readily appreciated that these communications may take place over a common channel or system bus.

Figure 2:
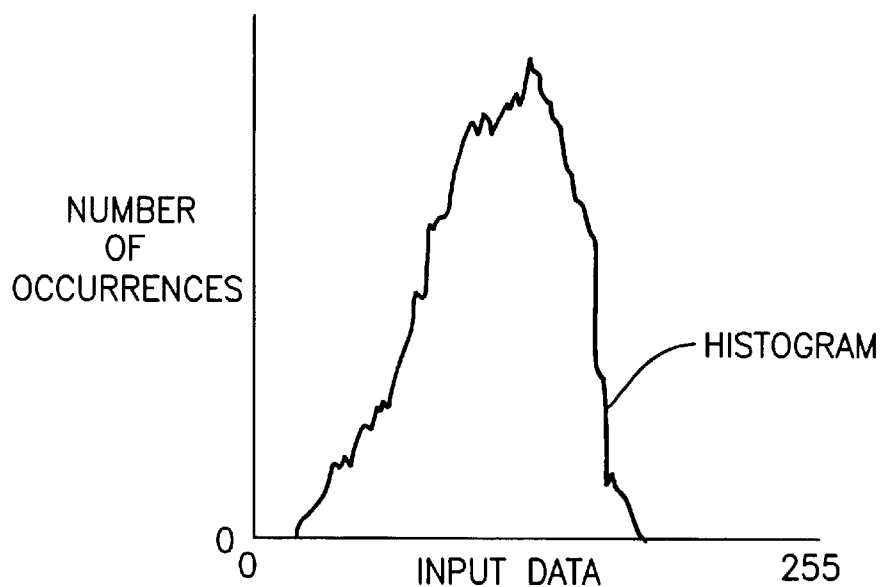
FIG. 2 is a graph representing a pixel intensity histogram, the pixel intensity values being plotted along the horizontal axis and the number of occurrences within each bin being plotted along the vertical axis.

In accordance with the preferred embodiment of the invention, the computer is programmed to retrieve succesive image frames of raw pixel intensity data from image processor 6 and then compute a respective histogram for each image frame. A typical pixel intensity histogram is shown in FIG. 2. Computing a histogram involves the steps of dividing the range of possible pixel intensity values into a series of non-overlapping bins of equal length, assigning each pixel intensity value in the image frame to a respective bin having that value, and counting the number of pixels in each bin for that image frame. FIG. 2 is a graph of the number of occurrences as a function of pixel intensity values. Successive histograms are stored in buffer memory in computer 8. The computer repeatedly compares the current histogram with the preceding histogram. If there is a large change from one histogram to the next, followed by a predetermined number of image frames showing a stabilized pixel intensity histogram, then the computer automatically re-optimizes the mapping and/or compression parameters and sends those re-optimized parameters to the image processor 6. The image processor 6 then uses those mapping parameters when it processes subsequent image frames of acoustic data.

Figure 3:
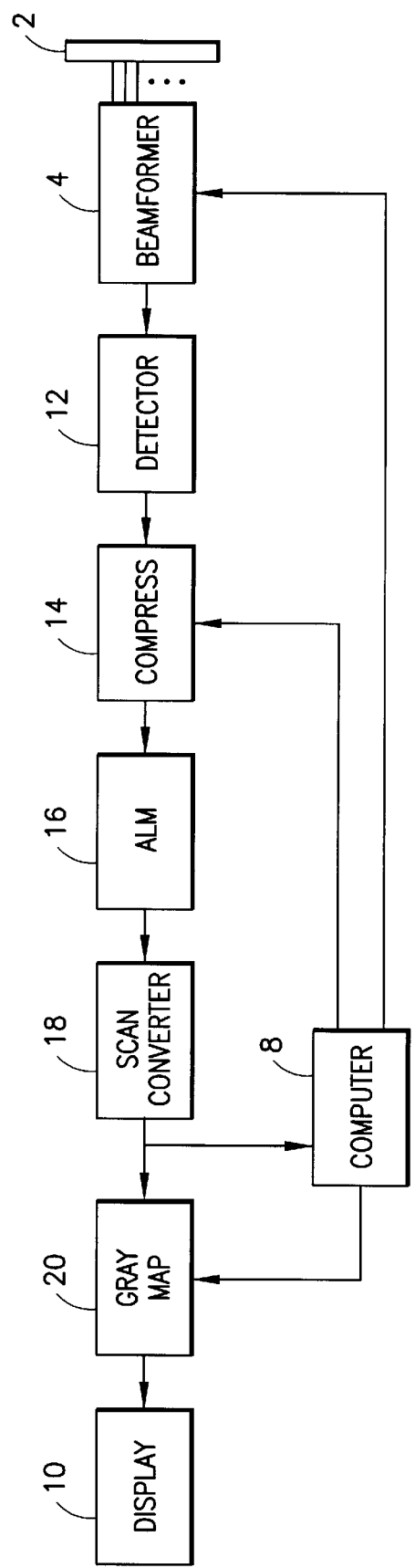
FIG. 3 is a block diagram showing in greater detail an ultrasound imaging system in accordance with the preferred embodiment of the invention.

Another preferred embodiment of the invention is shown in FIG. 3, which shows a signal path of a B-mode ultrasound imaging system. The received RF (or its equivlent I/Q pair) data output by the beamformer 4 is envelope detected by detector 12 on a vector-by-vector basis. Then the detected data is compressed in data compression block 14 (which preferably comprises a lookup table loaded by the computer 8 into a random access memory) to reduce the dynamic range for a pixel value (typically 8 bits) display. An acoustic line memory (ALM) 16 accumulates vectors of compressed acoustic data for one sweep across the array, to form a two-dimensional image. A scan converter 18 transforms the R-θ or X-Y acoustic data format into an X-Y pixel or video data format, thus forming the pixel intensity data. In the preferred embodiment, the image data to be analyzed is already in X-Y format. The pixel intensity data is then mapped into gray-scale values by the gray map 20 for display on monitor 10. Preferably the gray mapping also comprises a lookup table loaded into random access memory by the computer.

Figure 4A:
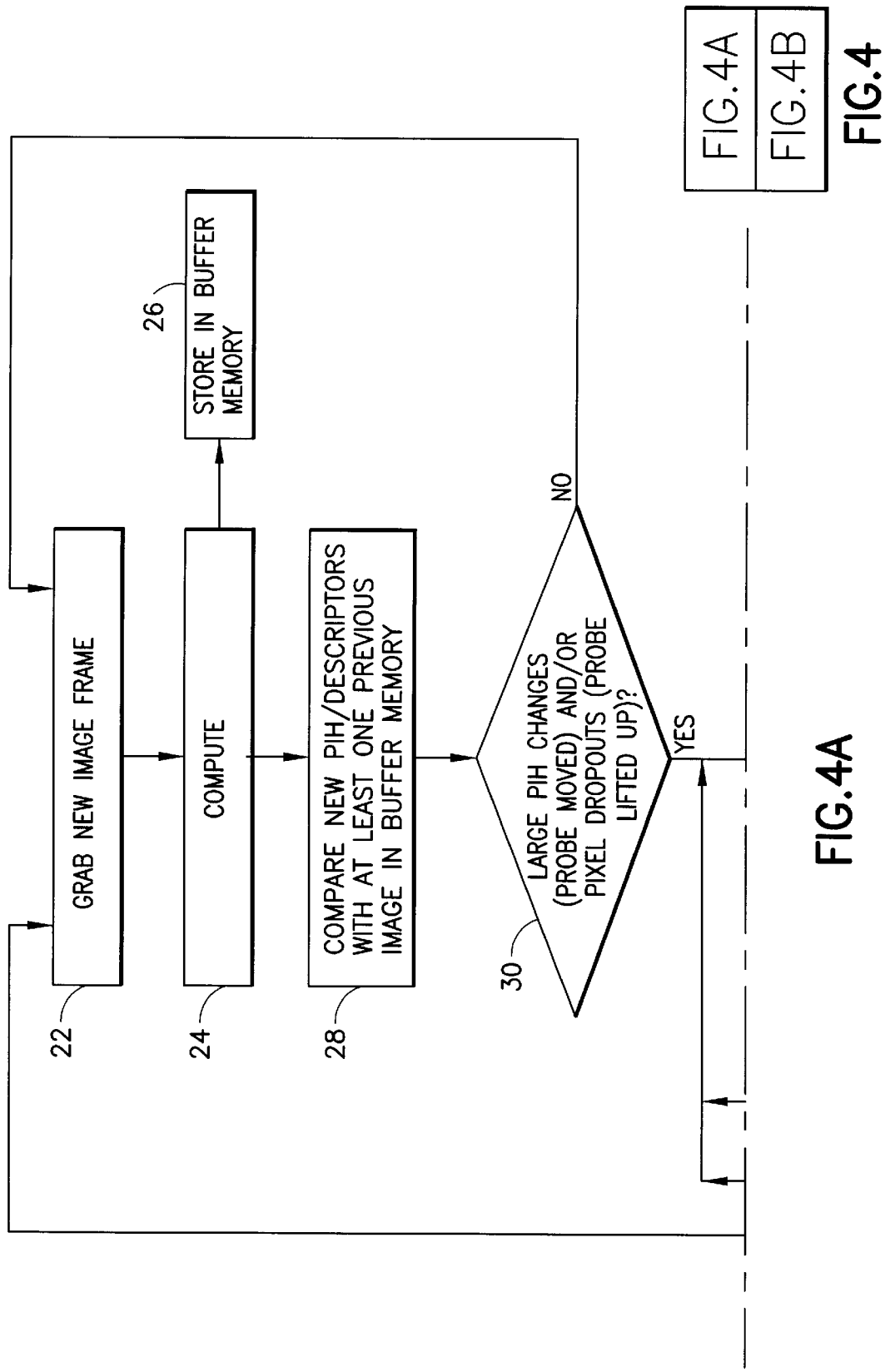
FIGS. 4A and 4B, is a flowchart showing the steps of a dynamic image optimizing algorithm in accordance with the preferred embodiment of the invention.
Figure 4B:
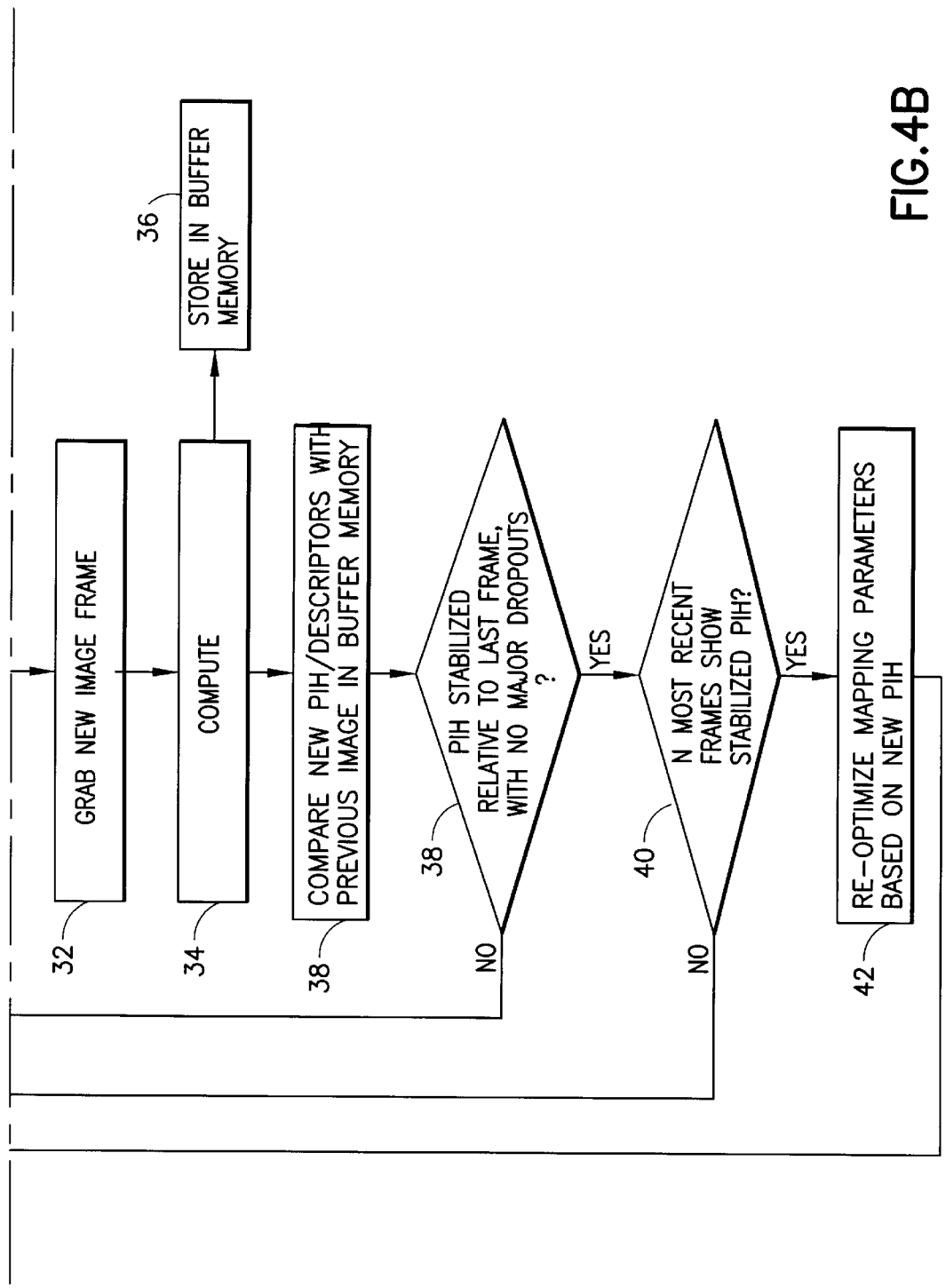

FIG. 4 shows a flowchart of the steps of the method in accordance with the preferred embodiment. In the first step 22, a new image frame is read out by the system computer either directly from the X-Y display memory in the scan converter (as shown in FIG. 3) or through a cine memory (not shown in FIG. 3). In the second step 24, the image pixel intensity histogram within a predefined ROI (e.g., a large central ROI within the image frame) is computed by counting the number of pixels that fall within each pixel value bin. For an 8-bit pixel display, the smallest pixel value is zero and the largest pixel value is 255. To reduce statistical variability, the pixel bin size of the pixel intensity histogram can be set larger than unity (e.g., 5). The pixel intensity histogram of that new image frame is stored in buffer memory (step 26), which already stores the pixel intensity histograms for previous image frames.

The next step in the process is to compare the histogram of the new image frame with the histogram of at least one previous image frames (step 28). This can be done using any of the standard statistical distribution descriptors, including the mean, standard deviation, skewness, and kurtosis. The p-th percentile point of the pixel intensity histogram is also a useful attribute. For example, the 5-th percentile point of the pixel intensity histogram may be very sensitive to image data dropouts (i.e., many pixels become zero) that occur when the probe is lifted off of the skin surface. In general, a combination of different histogram descriptors may be used, or even the entire histogram may be used to detect (step 30) when predetermined changes have occurred between the pixel intensity histogram (PIH) of at least one previous image frame and the pixel intensity histogram of the new image frame. If the changes in selected histogram attributes (e.g., the 5-th and 90-th percentile points) have not exceeded some predetermined threshold or thresholds, then the routine returns to step 22 and the process resumes the sequence of steps for the next image frame. If the changes in the selected histogram attributes exceed the predetermined threshold or thresholds, then the image is considered to have changed due to relative motion of the probe and the anatomy of interest. This initiates the next series of steps (starting with step 32 in FIG. 4) aimed at detecting when the image pixel intensity histogram becomes stable again (i.e., probe motion has subsided).

In step 32, a new image frame is read out by the system computer. The image pixel intensity histogram is within the predefined ROI is again computed (step 34) in the manner previously described with reference to step 24. Again the resulting pixel intensity histogram is stored in buffer memory (step 36). That histogram is then compared with the histogram of the previous image frame in step 38, using any of techniques previously described with reference to step 28. A combination of different histogram descriptors may be used, or even the entire histogram may be used to detect (step 40) when the pixel intensity histogram of the new image frame is stabilized relative to the pixel intensity histogram of the previous image frame with no major dropouts. If the changes in selected histogram attributes (e.g., the 5-th and 90-th percentile points) are not within some predetermined tolerance (preferably different than the threshold used in step 30), then the routine returns to step 32 and the process resumes the following sequence of steps for the next image frame. If the changes in the selected histogram attributes are with the predetermined tolerance, then step 42 is performed to determine whether the probe is not moving.

The criterion for triggering an image re-optimization, employed in step 42, is that the N most recent frames all show the same pixel intensity histogram statistics to within some predefined tolerance(s), wherein N is a positive integer greater than 2. The value of N may be based on the frame rate and a predefined amount of time (e.g., 2 sec). If the stability criterion is met, a re-optimization of the gray mapping function is executed. For example, the gray map can be scaled/shifted to map the upper and lower bounds of the pixel intensity histogram to some optimal upper and lower gray levels respectively. Such a gray map adjustment is basically known in the art, but will be described later in detail for the sake of completeness.

In addition, the mapping function may also include the data compression curve applied to each data vector in block 14 (see FIG. 3). This is typically a logarithmic function. For example, if the 90-th percentile point of the pixel intensity histogram is found to be approaching 255, the image display is likely to be saturated with blooming white pixels. In this case, the input dynamic range of the compression curve may be automatically increased to accommodate the large pixel values before further gray map adjustments are made.

Figure 5:
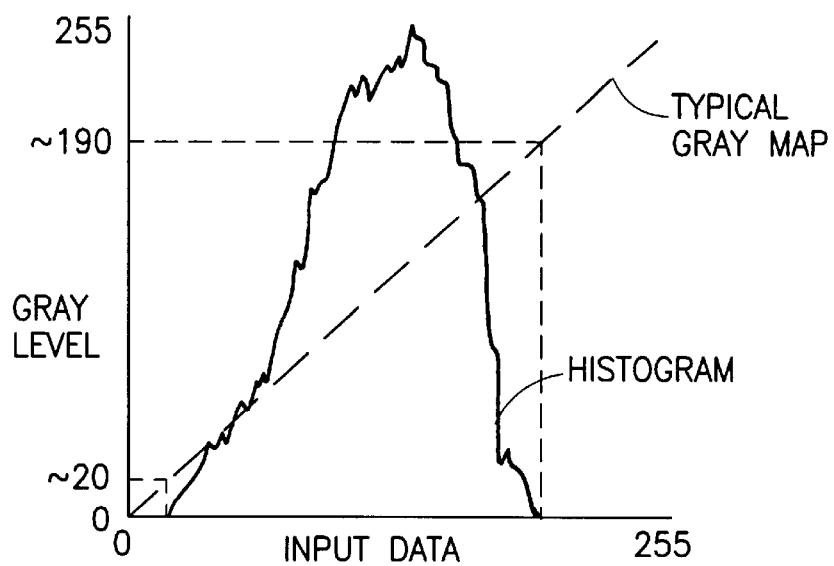
FIG. 5 is a graph showing a conventional gray map superimposed on the pixel intensity histogram of FIG. 2.

FIG. 5 shows a raw data histogram (indicated by the jagged solid line) with a typical gray map superimposed thereon (indicated by the dashed line). This typical gray map outputs a gray-scale value equal to the input value. Given the raw data and the gray map shown in FIG. 5, roughly 171 (20 through 190) gray-scale values out of 256 (0 to 255) are used. For this example, 67% of the gray-scale values are used. The ATO function is designed to provide a more optimal gray mapping in such circumstances.

In accordance with the preferred embodiment, the ATO function is automatically activated by the computer in response to detecting a sequence of pixel intensity histograms satisfying the foregoing conditions. When ATO is enabled, the gray mapping is re-optimized based upon certain characteristics of one or more pixel intensity histograms. Then the raw pixel intensity data is contrast adjusted by transforming each value into the corresponding gray-scale value established by the re-optimized mapping. The raw pixel intensity values outside the new gray map input range are mapped to a minimum (0) or a maximum (255) gray-scale value. As a result, the contrast of the raw pixel intensity data of greatest interest is increased.

To accomplish the foregoing, the computer 8 can utilize the last M pixel intensity histogram computed in performing the algorithm shown in FIG. 4, where M is any positive integer. Alternatively, the computer can construct a new pixel intensity histogram based on the pixel intensity data of a new image frame. The computer then determines the end points of the histogram by searching from each direction. The range of raw pixel intensity values between the end points is the map input range. The computer then compresses (or expands) an existing gray map to fit the new map input range, e.g., the end points 0 and 255 of the gray-scale value range are correlated to the end points of the map input range. Each raw pixel intensity value is then assigned a gray-scale value in accordance with this newly generated gray map. Alternatively, rather than searching for the absolute end (first non-zero input bin) from each direction, the search from each end can continue until some percentage of the raw pixel intensity data has been found. If different criteria are used at the lower and higher ends, this enables clipping of the raw pixel intensity data having the lowest and the highest values. In accordance with further variants, the end points of the histogram can be established by calculating the standard deviation of the data and finding the end points associated with a particular number of standard deviations. Rather than transforming the old map into the new map using the end points of the new map input range, it is possible to generate an entirely new map between the end points of the new map input range. Alternatively, a multiplicity of gray maps can be stored in memory, the computer selecting the most suitable one of the stored maps and sending it to the processor which performs the gray-scale mapping.

Figure 6:
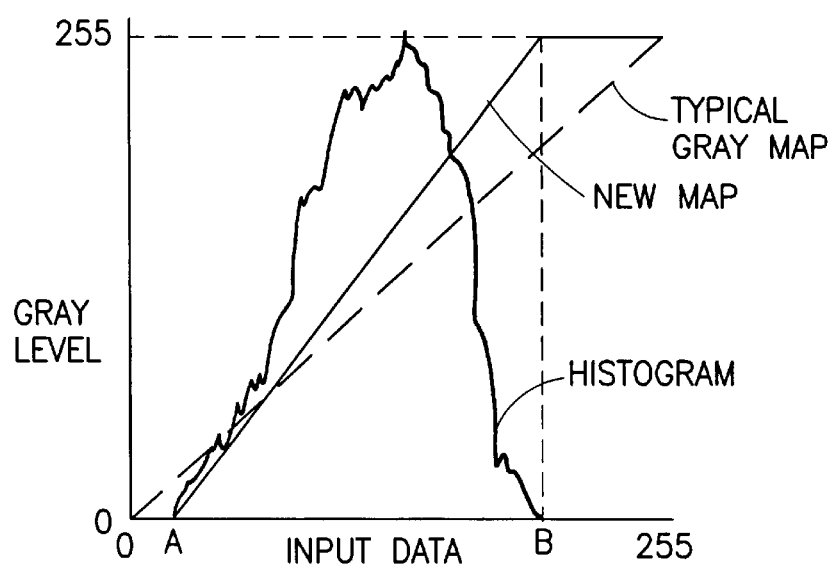
FIG. 6 is a graph showing an adaptively generated gray map superimposed on the same pixel intensity histogram.

As stated above, a new gray map can be generated by transforming an old gray map comprising a table of input and output values. In the case where the old map is a linear function (indicated by the dashed line in FIG. 6), the new map will also be a linear function (indicated by the straight solid line in FIG. 6). Alternatively, if the old map is a nonlinear function, then the new map generated from the old map will also be a nonlinear function. For example, if the old gray map is a nonlinear function, a map transformation algorithm is used to compress (or expand) that nonlinear function to fit within the new map input range, e.g., the range from A to B in FIG. 6.

More specifically, each input value $x_{new}$ of the new map is processed to arrive at a corresponding new map output value $y_{new}$. The computer performs the following steps.

If $x_{new}<A$, then $y_{new}=0$.

If $x_{new}>B$, then $y_{new}=255$.

If $A \leq x_{new} \leq B$, then $y_{new}=y_{old}$  (I)

where I is an index computed by the CPU based on the following equation:

$$\left(1 + \frac{256-(B-A)}{B-A}\right)(x_{new} - A) = I$$

where the number 256 represents the old map input range, and (B-A) represents the new map input range. The new map output value $y_{new}$ is obtained by inputting the index I into the old gray map to obtain the corresponding old map output value. The latter value is then transferred into the new map. This process is repeated until output values for all of the new map input values between the end values A and B have been derived from the old map. Using this technique, the old map can be compressed (or expanded) to fit within the new map input range determined from the raw data histogram.

Rather than searching for the absolute end (first non-zero input bin) from each direction, the search from each end can continue until some percentage of raw data is found. If different criteria are used at the lower and higher ends, this enables clipping of, for example, the lowest 5% of raw data and the highest 0.3% of raw data. This technique can be applied in the transformation of an old gray map (using the map transformation algorithm described above) or in the creation of a new gray map.

Alternatively, the end points can be established by calculating the standard deviation of the raw data and then finding the end points associated with a particular number of standard deviations. There is no restriction that the same criteria be used at each end.

Although the preferred embodiments have been described with reference to gray map generation by a host computer, it will be appreciated by persons skilled in the art that, in the alternative, the new gray map could be generated by dedicated hardware.

In accordance with another preferred embodiment, the data compression curve is automatically optimized (e.g., set to values which optimize contrast in the displayed image). This is preferably accomplished by writing a new data compression lookup table into random access memory in the data compression block. The host computer may select a suitable data compression lookup table from a multiplicity of prestored tables or may generate a new data compression lookup table. The data compression curve can be optimized by itself or in combination with optimization of the gray-scale mapping function.

The invention is not limited, however, to optimization of mapping or data compression parameters in response to detection of probe movement followed by probe stabilization. The imaging mode can also be controlled in this manner. For example, a zoom mode can be initiated whenever the pixel intensity histograms indicate that the probe has stabilized. Stabilization is presumed to mean that the sonographer has found an anatomical region of interest. In response to detection of probe stabilization, the host computer will adapt the transmit parameters so that a region of interest reduced in size is scanned, for example, by increasing the vector density and/or by increasing the number of transmit focal zones per unit depth within the region of interest and not scanning outside the region of interest. The computer may be programmed to automatically return the system to a non-zoom mode when probe movement is resumed. Alternatively, the zooming effect can be achieved by scaling a region of interest in an image frame.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

As used in the claims, the term "(N+1) most recent image frames" means (N+1) image frames acquired successively in time, the oldest image frame being the (N+1)-th most recent image frame and the newest image frame being the first most recent image frame.

What is claimed is:

1. An ultrasound imaging system comprising a computer programmed to re-optimize a set of operating parameters automatically in, response to detection of the following conditions:

(a) the N most recent image frames have pixel intensity histograms which are stabilized; and (b) the (N+1)-th and said N-th most recent image frames have pixel intensity histograms which are different to at least a prestored degree.

2. The system as recited in claim 1, wherein said set of operating parameters comprise gray mapping values.

3. The system as recited in claim 2, wherein gray mapping values are re-optimized in dependence on a measured characteristic of at least one stabilized pixel intensity histogram.

4. The system as recited in claim 1, wherein said set of operating parameters comprise data compression values.

5. The system as recited in claim 1, wherein said set of operating parameters comprise beamforming time delays.

6. The system as recited in claim 1, wherein said set of operating parameters comprise scaling values.

7. The system as recited in claim 1, wherein said computer compares pixel intensity histograms using one or more statistical distribution descriptors.

8. The system as recited in claim 7, wherein said one statistical distribution descriptor is a mean.

9. The system as recited in claim 7, wherein said one statistical distribution descriptor is a standard deviation.

10. The system as recited in claim 7, wherein said one statistical distribution descriptor is skewness.

11. The system as recited in claim 7, wherein said one statistical distribution descriptor is kurtosis.

12. The system as recited in claim 7, wherein said one statistical distribution descriptor is a p-th percentile point.

13. A method for automatically re-optimizing a set of operating parameters in an ultrasound imaging system, comprising the steps of:

(a) computing a respective pixel intensity histogram for each one of (N+1) most recent image frames;

(b) determining whether a first condition is satisfied, said first condition being that the N-th and (N+1)-th most recent image frames have pixel intensity histograms which are different to at least a predetermined degree;

(c) if said first condition is satisfied, determining whether a second condition is satisfied, said second condition being that the N most recent image frames have pixel intensity histograms which are stabilized; and (d) re-optimizing a set of operating parameters in response to said first and second conditions being satisfied.

14. The method as recited in claim 13, wherein said set of operating parameters comprise gray mapping values.

15. The method as recited in claim 14, wherein gray mapping values are re-optimized in dependence on a measured characteristic of at least one stabilized pixel intensity histogram.

16. The method as recited in claim 13, wherein said set of operating parameters comprise data compression values.

17. The method as recited in claim 13, wherein said set of operating parameters comprise beamforming time delays.

18. The method as recited in claim 13, wherein said set of operating parameters comprise scaling values.

19. The method as recited in claim 13, further comprising the step of comparing pixel intensity histograms using one or more statistical distribution descriptors.

20. An ultrasound imaging system comprising:

means for computing a respective pixel intensity histogram for each one of (N+1) most recent image frames;

means for determining whether a first condition is satisfied, said first condition being that the N-th and (N+1)-th most recent image frames have pixel intensity histograms which are different to at least a predetermined degree;

means for determining whether a second condition is satisfied, said second condition being that the N most recent image frames have pixel intensity histograms which are stabilized; and means for re-optimizing a set of operating parameters in response to said first and second conditions being satisfied.

21. The system as recited in claim 20, wherein said set of operating parameters comprise gray mapping values.

22. The system as recited in claim 21, wherein gray mapping values are re-optimized in dependence on a measured characteristic of at least one stabilized pixel intensity histogram.

23. The system as recited in claim 20, wherein said set of operating parameters comprise data compression values.

* * * * *